United States Patent
Scherer et al.

(12) 
(10) Patent No.: US 6,440,411 B2
(45) Date of Patent: Aug. 27, 2002

(54) OPHTHALMIC PRODUCT COLORED WITH BLUE ALGA EXTRACT

(75) Inventors: Anton Scherer, Frammersbach; Peter Schwind, Hösbach-Rottenberg, both of (DE)

(73) Assignee: Novartis, AG, Basel (CH)

( * ) Notice: Subject to any disclaimer, the term of this patent is extended or adjusted under 35 U.S.C. 154(b) by 0 days.

(21) Appl. No.: 09/838,439

(22) Filed: Apr. 19, 2001

(30) Foreign Application Priority Data

Apr. 20, 2000 (EP) .......................................... 00108597

(51) Int. Cl.⁷ ........................ A61K 38/44; A61K 35/80; A61K 9/20; A61L 2/00; B08B 3/00
(52) U.S. Cl. ................................ 424/94.4; 424/195.17; 424/464; 422/28; 134/27; 134/901; 510/114
(58) Field of Search ................................ 424/94.4, 780, 424/195.17, 464; 510/114; 422/28; 134/27, 901

(56) References Cited

U.S. PATENT DOCUMENTS

| | | | | |
|---|---|---|---|---|
| 4,396,583 A | * | 8/1983 | LeBoeuf | 422/301 |
| 5,630,884 A | * | 5/1997 | Huth | 134/27 |
| 6,099,800 A | * | 8/2000 | Cheng | 422/30 |
| 6,113,886 A | * | 9/2000 | Bryan | 424/49 |

FOREIGN PATENT DOCUMENTS

| | | | |
|---|---|---|---|
| JP | 54101833 | | 8/1979 |
| JP | 63-120762 | * | 5/1988 |
| JP | 09-294596 | * | 11/1997 |
| WO | WO 97/18288 | | 5/1997 |
| WO | WO 97/29319 | | 8/1997 |

OTHER PUBLICATIONS

Akhilender et al., "Toxicity assessment of phycocyanin—A blue colorant from glue green alga *Spirulina plantensis*", Food Biotechnology 13 (1):51–66 (1999).*

* cited by examiner

*Primary Examiner*—Sandra E. Saucier
(74) *Attorney, Agent, or Firm*—R. Scott Meece; Jian S. Zhou; Richard I. Gearhart

(57) ABSTRACT

The present invention is directed to an ophthalmic product comprising, as a colouring agent, the extract of an alga. A preferred class of alga the extract of which is useful in the present invention is blue alga (Spirulina type), more preferred it is Japanese blue alga (*Spirulina platensis*). The ophthalmic product is preferably a contact lens care product.

6 Claims, No Drawings

OPHTHALMIC PRODUCT COLORED WITH BLUE ALGA EXTRACT

The present invention is directed to an ophthalmic product comprising, as a colouring agent, the extract of an alga. A preferred class of alga the extract of which is useful in the present invention is blue alga (Spirulina type), more preferred it is Japanese blue alga (*Spirulina platensis*). The ophthalmic product is preferably a contact lens care product.

BACKGROUND OF THE INVENTION

A few ophthalmic products comprising a colouring agent are known, inter alia the vitamin B12 comprising products according to EP-A-555,464 wherein said vitamin B12 provides a rose colour. However, the known products are having some disadvantages which are overcome by the products of this invention. The ophthalmic products according to this invention comprise a natural colouring agent, harvested from naturally grown plants. Said colouring agents are useful for providing an intense and long-lasting tint to ophthalmic solutions. However, articles treated with such ophthalmic solution, such as a contact lens, are not tinted by this colouring agent in a manner visible to the naked eye. This is due, inter alia, to the typically high molecular weight of the algae extracts, which molecular weight is well above 200,000 in the case of the *Spirulina platensis* extract.

SUMMARY OF THE INVENTION

One aspect of the invention is an ophthalmic product comprising, as a colouring agent, the extract of an alga. Said extract is preferably blue or green, more preferred blue. Said alga is preferably a blue alga of the Spirulina type. It is also preferred to obtain the extract from a Spirulina type alga, even more preferred from the Japanese blue alga (*Spirulina platensis*). Other known Spirulina species are *Spirulina gigantea* or *Spirulina maxima*. Typical extracts which are useful as colouring agents in the context of this invention are Lineablue A (about 30% Phycocyanin), Lineablue HK (about 60% Phycocyanin) and Lineablue HG (about 70% Phycocyanin), all of which are marketed by Dainippon Ink & Chemicals Inc., Japan. Another suitable product is Spirulina blue distributed by Tokai Saga Co. Ltd, Japan.

Another way of defining the colouring agent which is used according to this invention is that said colouring agent comprises a certain amount of Phycocyanin. Thus, the colouring agent which is comprised in the ophthalmic product of claim 1 alternatively can be defined as comprising at least about 10% of Phycocyanin, more preferred at least about 25% of Phycocyanin, but higher percentages are possible and In line with this Invention.

The ophthalmic product of this invention comprises eyedrops, eye washes, eye medicaments, and said ophthalmic product preferably is a contact lens care product. This term is understood to comprise products for treating contact lenses for various purposes, for example for storing, maintaining, disinfecting, or cleaning contact lenses. Further the term contact lens product comprises liquids, gels, powders, tablets or combinations thereof. In case of a combination of, for example, a liquid and a tablet, it is sufficient for the purpose of this invention if only the liquid comprises the extract of an alga, or if only the tablet comprises the extract of an alga. In the case of combinations, also the term two-component product is used hereinafter.

DETAILED DESCRIPTION OF THE PREFERRED EMBODIMENTS

The preferred ophthalmic product of this invention, a contact lens care product, can be virtually any of the known contact lens products to which an algae extract has been added. Thus, said contact lens care product may comprise any of the conventional ingredients typically used in this technical field, such as tonicity agents (for example salts, e.g. sodium chloride, or non-ionic compounds, e.g. glycerol, mannitol or lactose), buffering agents (e.g. borate, phosphate or TRIS buffers, such as sodium phosphate buffers), preservatives (e.g. benzalkonium chloride), conditioning or wetting agents (e.g. polyvinylalcohol, poloxamers, polyvinylpyrrolidone, hydroxypropylmethylcellulose), lubricating agents (e.g. polyalkylene glycols), antifoaming agents (e.g. simeticon, which is a 30% silicon oil/water emulsion), disinfecting agents (e.g. hydrogen peroxide, polyhexamethylenebiguanides, quatemary ammonium salts), stabilizing agents (e.g. agents stabilizing hydrogen peroxide such as Dequest compounds), agents decomposing disinfecting agents (e.g. platinum, catalase, pyruvate, sodium thiosulfate), enzymes (e.g. subtilisin, pancreatin, papain), coating agents (e.g. Methocel, polyvinylpyrrolidone).

The main purpose of having added an extract of an alga, which provides a colour, to an ophthalmic product is to enable the patient intending to use said ophthalmic product to make a determination whether or not said product is actually being used. It is evident that said determination can be made more easily when a blue product is used compared to a colourless one. This main purpose Is even more pronounced in case a two-component ophthalmic product is being used of which product one component does have no colour, while the other component comprises such an alga extract.

A more specific embodiment of the invention is therefore directed to a two-component ophthalmic product at least one component of which, more preferably only one component of which comprises, as a colouring agent, an extract of an alga. The principle of this invention can be applied also to oligo-component products having more than two components.

Typical examples of two-component products are products comprising two liquids in separate containers, or products comprising a liquid in a first container and tablets packed separately therefrom. More specifically, such two-component products may be represented by lens care products which comprise a disinfecting agent in a first bottle, such as hydrogen peroxide, and a hydrogen peroxide decomposing liquid in a second bottle, such as a catalase solution. Another two-component product is represented by a contact lens care product which comprises a disinfecting agent in a first bottle, such as hydrogen peroxide, and one or more tablets for decomposing hydrogen peroxide e.g. in a blister pack, for example catalase tablets. In a preferred embodiment of the invention, only one component of the two components comprises the alga extract, typically the component to be used second. Thus, in the above examples, it would be the catalase solution, or the catalase tablet, comprising the alga extract, not the disinfecting solution.

A preferred embodiment of this invention is a two-component product comprising a disinfecting liquid, such as a peroxide solution, and a tablet which tablet comprises an agent decomposing the disinfecting agent as well as the alga extract. Application of such a product by the end-user makes it easy for the user to determine whether or not the tablet has been dissolved already in the disinfecting agent, by presence or absence of the colour.

The preferred product of this invention is a two-component product comprising a hydrogen peroxide solution and tablets comprising catalase wherein said tablets also comprise the alga extract. Even more preferred said tablet is a retarded tablet which releases the catalase only after a predetermined period of time.

Such two-component products are known In the art but without the alga extract. In addition to this, the two-component products of this invention preferably comprise a hydrogen peroxide solution which is not acidic, but buffered to a neutral pH, or very close to a neutral pH. Neutral pH is understood to comprise the pH range between 6 and 8, more preferably between 6.4 and 7.6, even more preferred between 6.7 and 7.3. In such a case it is a further advantage of this invention that the tablet, to be used with such buffered hydrogen peroxide solution, may not require a buffer, or can be totally free of any buffering system. In case the peroxide solution is buffered to a pH which is very close to a neutral pH, for example to a pH of 5.5 to 6.5, or more preferred to a pH of 5.8 to 6.2, especially to a pH of 6.0, the tablet to be used with such a buffered hydrogen peroxide still does not require a buffer, but an amount of a basic component for adjusting the pH to a neutral pH may be included in the tablet. Such a basic component may be for example trisodiumphosphate in an amount which raises the pH of those few milliliters of hydrogen peroxide which are being used for disinfection of a pair of contact lenses from e.g. 6.0 to neutral, such as 7.2.

Retardation of tablets to be used in such systems has been disclosed in the art. However, it has been found very useful to apply a coating comprising at least three layers in order to control release time or retardation time, respectively. Thus, a preferred tablet in a two-component product as disclosed herein is a tablet the coating of which comprises three layers, one of which is of the Eudragit type (typically a methacrylic acid—ethyl acrylate copolymer). Even more preferred the coating has an Eudragit type component as the middle layer, while the first and third layer (or the inner and outer layer) are being composed of other coating agents, such as Pharmacoat.

A preferred tablet has a first outer Pharmacoat layer which comprises e.g. an antifoaming agent and which acts as a barrier, then a middle layer of Eudragit providing the desired retarding time, and an Inner Pharmacoat layer which typically comprises the alga extract Said inner layer essentially prevents the direct contact of the peroxide with catalase during the retardation period.

Tablets as disclosed herein do have the advantage over tablets known in the art that the retarding effect lasts for up to and even more than 30 minutes, or up to and more than 45 minutes, while commercially available systems typically retard only for a few minutes if at all. This longer retarding time which can be easily adjusted according to this invention to an average of 45 minutes is beneficial because it guarantees a high level of disinfection. This can be demonstrated by very good microbiological data.

The longer exposure time of a contact lens to a disinfecting solution can be recommended based on the fact that the disinfecting solution is buffered. Contact lenses are much less exposed to physical stress in a buffered, pH neutral hydrogen peroxide solution, while in a typical acidic hydrogen peroxide solution they are exposed, the result being a change of physical design, which is reshaped after neutralisation. This process if happening too often clearly would have negative consequences on shelf-life of the contact lenses.

While it is relevant to the preferred embodiment of the invention that a buffer is present in the hydrogen peroxide solution, but not in the tablet, other conventional additives known to be used in contact lens care products may be used, as well as conventional coating additives, at the discretion of the person skilled in the art.

The following examples are for illustration purposes only, and are not intended to be limiting the invention in any manner.

EXAMPLE 1

A tablet for use with a buffered to neutral hydrogen peroxide solution, such as AOSept solution, is having the following composition:

Core: Catalase from Corynebacter, lyophilized, Maltodextrin DE2, Mannitol, potassium carbonate, macrogolum 6000, silicium dioxide of high dispersity, Japanese blue alga colour (colouring extract from *Spirulina platensis*)

Coating: Pharmacoat, Eudragit L 30 D-55, Macrogolum 6000, Simethicon 30%, Japanese blue alga colour (colouring extract from *Spirulina platensis*).

The coating is a triple layer, the first inner layer on the core being Pharmacoat and colouring extract, followed by a middle layer of Eudragit, the upper layer again being Pharmacoat and Simeticon.

EXAMPLE 2

A two component product comprising a Solution and a Tablet is composed as

Solution:
3.5% hydrogen peroxide,
0.136% Sodium dihydrogen phosphate,
0.062% Disodium hydrogen phosphate,
0.8% sodium chloride,
0.012% Dequest 2060,
aqua purificata ad 100%.
Said solution has a pH of 6.0.

Tablet:
Core: Catalase lyophilisate 0.441 mg (about 11 0000 I.U.), lactose monohydrate 44.5 mg, trisodiumphosphate anhydrate 15.0 mg, Macrogolum 6000 2.029 mg, Pharmacoat 603 2,000 mg, Simeticon (30%) 0.1 mg.

Coating: Pharmacoat 603 6.5 mg, Lineablue A (Japanese blue alga extract about 30%) 2 mg, Eudragit L 30 D-55 4.00 mg, Macrogolum 6000 1.00 mg, Simeticon (30%) 0.3–0.4 mg.

What is claimed is:

1. An ophthalmic product comprising,
a hydrogen peroxide disinfecting solution and
a tablet comprising catalase for the decomposition of the disinfecting solution and an extract of a blue alga as a colouring agent.

2. The product of claim 1, wherein said blue alga is Japanese blue alga *Spirulina platensis*.

3. The product of claim 1 wherein the hydrogen peroxide disinfecting solution is buffered.

4. The product of claim 1, wherein the tablet comprises a coating of at least three layers.

5. An ophthalmic product according to claim 4, wherein the inner one of the three layers comprises the extract of the blue alga.

6. An ophthalmic product according to claim 1, wherein the tablet is devoid of a buffer.

* * * * *